(12) United States Patent
Zhao et al.

(10) Patent No.: US 6,703,444 B2
(45) Date of Patent: Mar. 9, 2004

(54) PROCESS FOR CROSS-LINKING HYALURONIC ACID TO POLYMERS

(75) Inventors: Xiaobin Zhao, Edinburgh (GB); Catherine Alexander, Gorebridge (GB); Jane Fraser, Carluke (GB)

(73) Assignee: A-Life Limited (GB)

( * ) Notice: Subject to any disclaimer, the term of this patent is extended or adjusted under 35 U.S.C. 154(b) by 0 days.

(21) Appl. No.: 09/924,182

(22) Filed: Aug. 2, 2001

(65) Prior Publication Data

US 2002/0049281 A1 Apr. 25, 2002

Related U.S. Application Data

(63) Continuation of application No. PCT/GB00/00316, filed on Feb. 3, 2000.

(30) Foreign Application Priority Data

Feb. 5, 1999 (GB) .............................................. 9902652

(51) Int. Cl.[7] .................................................. C08F 8/00
(52) U.S. Cl. ................... 525/61; 525/54.2; 524/500; 524/29; 424/423; 424/488; 424/449; 536/41; 536/55.1; 536/4.1; 514/54; 514/777
(58) Field of Search ............... 514/54, 777; 536/41, 536/55.1, 4.1; 524/500, 29; 424/423, 488, 449; 525/54.21, 61

(56) References Cited

U.S. PATENT DOCUMENTS

| 4,582,865 A | 4/1986 | Balazs et al. ................. 524/29 |
| 5,411,874 A | 5/1995 | Ellwood et al. .............. 435/84 |
| 5,510,121 A | 4/1996 | Rhee et al. ................. 424/520 |
| 5,550,187 A | 8/1996 | Rhee et al. ................ 525/54.1 |
| 5,578,661 A | 11/1996 | Fox et al. ..................... 524/27 |
| 5,644,049 A | 7/1997 | Giusti et al. .................. 536/53 |
| 5,677,276 A | 10/1997 | Dickerson et al. ............. 514/8 |
| 5,800,541 A | 9/1998 | Rhee et al. ................... 623/11 |

FOREIGN PATENT DOCUMENTS

| EP | 0 161 887 A2 | 11/1985 |
| WO | WO 97/04012 | 2/1997 |
| WO | WO 98/02204 | 1/1998 |
| WO | WO 9802204 A1 * | 1/1998 .......... A61M/29/00 |

OTHER PUBLICATIONS

Survey of Organic Syntheisi, Calvin Buehler and Donald Pearson, 1970, p. 802.*
U.S. Publication No. US 2002/0091251 A1; "Process for the Production of Multiple Cross–Linked Hyaluronic Acid Derivatives"; published Jul. 11, 2002; Xiaobin Zhao.
Hardingham, T.E. and Muir, H., "The specific interaction of hyaluronic acid with cartilage proteoglycans," *Biochim. Biophys. Acta* 279:401–405, Elsevier Publishing Company (1972).
Tomihata, K. and Ikata, Y., "Crosslinking of hyaluronic acid with water–soluble carbodiimide," *J. Biomed Mater. Res.* 37:243–251, John Wiley and Sons, Inc. (Nov. 1997).
English language abstract of Japanese Publication NO. 08157378, JPO (1996).

* cited by examiner

*Primary Examiner*—David W. Wu
*Assistant Examiner*—Satya Sastri
(74) *Attorney, Agent, or Firm*—Sterne, Kessler, Goldstein & Fox, P.L.L.C.

(57) ABSTRACT

The present invention relates to a process for the production of hyaluronic acid (HA) derivatives. In particular, the process relates to multiple cross-linked hyaluronic acid derivatives, to navel cross-linked derivatives so obtained, and to products containing them and their uses in cosmetic, medical and pharmaceutical applications.

26 Claims, No Drawings

PROCESS FOR CROSS-LINKING HYALURONIC ACID TO POLYMERS

This application is a continuation of International Application No. PCT/GB00/00316, filed on Feb. 3, 2000, which was published under PCT Article 21(2) in English and which is fully incorporated herein by reference, which claims priority to foreign application number 9902652.8, filed on Feb. 5, 1999 in Great Britain.

The present invention relates to a process for the production of hyaluronic acid (HA) derivatives, in particular multiple eg double cross-linked hyaluronic acid derivatives, and to novel cross-linked derivatives so obtained, to products containing them and their uses in cosmetic, medical and pharmaceutical applications.

HA is a member of a class of polymers known as glycosaminoglycans. HA is a long chain linear polysaccharide and is usually present as the sodium salt which has a molecular formula of $(C_{14}H_{20}NNaO_{11})_n$ where n can vary according to the source, isolation procedure and method of determination. However, molecular weights of up to $14 \times 10^6$ have been reported.

HA and its salts can be isolated from many sources including human umbilical cord, rooster combs and nearly all connective matrices of vertebrate organisms. HA is also a capsular component of bacteria such as Streptococci as was shown by Kendall et al, (1937), *Biochem. Biophys. Acta*, 279,401–405; it may therefore also be obtained by fermentation methods. For example, the present applicant's U.S. Pat. No 5,411,874 describes a method for producing hyaluronic acid by continuous fermentation of *Streptococcus equi*.

HA is non-immunogenic and therefore has great potential in medicine. Because of its visco-elastic properties HA having a high molecular weight (over 1 million) has been found to be particularly useful in a variety of clinical fields, including wound treatment, ophthalmic surgery and orthopaedic surgery. HA is also potentially useful in a variety of non-medical fields, such as cosmetic applications.

However, the use of HA in certain of these applications is limited by the fact that following administration to humans HA is readily degraded by enzymes such as hyaluronidases and free radicals. Furthermore, HA is soluble in water at room temperature, which can also make it less suited to certain applications. Various attempts have therefore been made to prepare more stable forms of HA, in particular by cross-linking the HA molecules.

Thus, U.S. Pat. No. 4,582,865 (Biomatrix Inc.) describes the preparation of cross-linked gels of hyaluronic acid which are formed by cross-linking HA either by itself or mixed with other hydrophilic polymers using divinyl sulfone as the cross-linking agent. It appears that in this case the cross-linking occurs via the hydroxyl groups of HA.

U.S. Pat. No. 5,550,187 (Collagen Corporation) describes a method for preparing cross-linked biomaterial compositions which involves mixing a biocompatible polymer, which is preferably collagen but may be selected from other polymers including hyaluronic acid, with a sterile dry cross-linking agent such as a synthetic hydrophilic polymer.

U.S. Pat. No. 5,510,121 (Rhee et al.) describes conjugates formed by covalently binding glycosaminoglycans or derivatives thereof to hydrophilic synthetic polymers, in particular activated PEG derivatives. The process described appears to involve only one cross-linking step.

U.S. Pat. No. 5,578,661 (Nepera Inc.) describes a gel forming system for use as a wound dressing which is formed from three main components, the first being a water soluble polymer, the second being an acid-containing polymer and the third being a polysaccharide or amino-containing polymer such as hyaluronic acid In this case the cross-linking appears to be via ion-bonding.

U.S. Pat. No. 5,644,049 (Italian Ministry for Universities and Scientific and Technology Research) describes a biomaterial comprising an inter-penetrating polymer network (IPN) wherein one of the polymer components is an acidic polysaccharide such as hyaluronic acid and the second polymer component may be a synthetic chemical polymer. The two components may be (but are not necessarily) cross-linked.

Tomihata and Ikada have reported cross-linking of HA using a water soluble carbodiimide as cross-linking agent. It was postulated that cross-linking took place via ester groups. The cross-linking reaction was also carried out in the presence of L-lysine methyl ester, which appeared to give additional cross-linking via amide bonds to the lysine ester. (J.Biomed.Mater.Res., 37,243–251,1997).

U.S. Pat. No 5,800,541 describes collagen-synthetic polymer matrices prepared using a multiple step reaction. The first step involves reacting collagen with a synthetic hydrophilic polymer, the resulting matrix may then be modified in a second reaction step which may involve cross-linking or conjugating the matrix with a synthetic polymer, coupling biologically active molecules or glycosaminoglycans to the matrix, cross-linking the matrix using conventional chemical cross-linking agents or modifying the collagen in the matrix by means of chemical reaction. In this process, the initial collagen-synthetic polymer matrix appears to be cross-linked via only one type of bond, and the additional process steps serve to introduce further chemical substances which may form different types of bonds. However, it does not appear that any two of the substances forming the product will be linked to each other by more than one type of bond.

International patent application WO 97/04012 (Agerup) describes polysaccharide (which may be inter alia hyaluronic acid) gel compositions which are prepared by forming an aqueous solution of the polysaccharide, initiating cross-linking in the presence of a polyfunctional cross-linking agent, sterically hindering the cross-linking reaction from being terminated before gelation occurs (eg by diluting the solution) and then reintroducing sterically unhindered conditions (eg by evaporating the solution) so as to continue the cross-linking to a viscoelastic gel. There is no suggestion in this application that different types of bonds are formed in the two cross-linking stages.

None of the aforementioned documents describe products in which HA is linked to one or more polymer molecules (which may be the same or different) by means of two different types of cross-linking bonds.

We have now found that hyaluronic acid may be cross-linked with other polymers by two different types of cross-linking bonds, to effect a 'double cross-linking'. The formation of different types of bonds is achieved by effecting the cross-linking via different functional groups. The bonds so formed can therefore be described as functional bonds. Thus, for example one type of bond may be formed by cross-linking via hydroxyl groups and a different functional bond formed by cross-linking via e.g. carboxyl groups. Such multiple cross-linking has been found to result in a high degree of cross-linking with improved biostability of HA based on the degree of crosslinking and selection of the second polymer.

In a first aspect therefore, the present invention provides a process for the preparation of multiple (e.g. double)

cross-linked derivatives of hyaluronic acid, which process comprises cross-linking HA to one or more polymers other than HA and optionally to another molecule of HA via two or more different functional groups.

The crosslinking of each type of functional group may be effected by contacting HA and at least one other polymer, with one or more cross-linking agents, simultaneously or sequentially, as described in more detail hereinbelow.

In this specification the polymer to which HA may be cross-linked will be referred to generally as "polymer", "second polymer" or "subsequent polymer". A "second polymer" or "subsequent polymer" may comprise a mixture of polymers.

In this specification, 'multiple crosslinked HA' refers to a hyaluronic acid derivative wherein a molecule of HA is cross-linked to a second polymer and optionally to a subsequent polymer and/or another molecule of HA by means of two or more different types of functional bond. Similarly, 'double crosslinked HA' refers to a hyaluronic acid derivative wherein a molecule of HA is cross-linked to a second polymer and optionally to a subsequent polymer and/or another molecule of HA by means of two different types of functional bond and 'single crosslinked HA' refers to a hyaluronic acid derivative wherein a molecule of HA is cross-linked only to a second polymer by only one type of functional bond.

Polymers to which HA may be cross-linked according to the present invention include biopolymers and synthetic polymers. It will of course be appreciated that the said polymer should be non-toxic and biocompatible. Preferably, the second (or subsequent) polymer is a water-soluble polymer. It will also be appreciated that the properties of the second (or subsequent) polymer will to some extent influence the properties of the final cross-linked product. The second or subsequent polymer should therefore be selected having regard to the properties desired in the final product, and should be compatible with and even enhance these properties. In particular, the second (or subsequent) polymer will preferably have good biostability.

Synthetic polymers which may be employed include polyvinyl alcohol (PVA), polyethylene oxide (PEO), and polypropylene oxide (PPO), as well as copolymers of any of the aforementioned polymers, polyacrylic acid, polyacrylamide and other hydroxyl, carboxyl and hydrophilic synthetic polymers.

Biopolymers which may be employed according to the present invention include polypeptides, cellulose and its derivatives such as hydroxyethyl cellulose and carboxymethyl cellulose, alginate, chitosan, lipid, dextan, starch, gellan gum and other polysaccharides.

The aforementioned polymers may be non-ionic, anionic or cationic. Non-ionic polymers include PVA, PEO and copolymers such as PEO—PPO—PEO. Cationic polymers include chitosan; amino-containing polymers, collagen and gelatin. Anionic polymers include alginate, gellan gum, carboxylmethyl cellulose (CMC), polyacrylic acid and polyaspartic acid.

It will be appreciated that certain polymers, for example polypeptides, may exist in either anionic or cationic form, depending on various factors, for example the pH of the reaction mixture. It is generally preferred to use such polymers under conditions which render them anionic.

The crosslinking of each type of functional group may be effected simultaneously or sequentially as described in more detail hereinbelow.

The functional groups which are mainly responsible for cross-linking of HA molecules to the second polymer are the hydroxyl and carboxyl groups. Hydroxyl groups may be cross-linked via an ether linkage and carboxyl groups via an ester linkage. If desired the HA may be chemically modified prior to cross-linking to form other chemically reactive groups. Thus for example HA may be treated with acid or base such that it will undergo at least partial deacetylation, resulting in the presence of free amino groups. Said amino groups may be cross-linked via an amide (—C(O)—NH—); imino (—N=CH—) or secondary amine (—NH—CH—) bond. An imino bond is a precursor of an amine bond and an imino linkage can be converted into an amine linkage in the presence of a reducing agent.

Cross-linking agents which may be used in the process of the present invention include those well-known in the art, for example formaldehyde, glutaraldehyde, divinyl sulfone, a polyanhydride, a polyaldehyde, a polyhydric alcohol, carbodiimide, epichlorohydrin, ethylene glycol diglycidylether, butanediol diglycidylether, polyglycerol polyglycidylether, polyethylene glycol diglycidylether, polypropylene glycol diglycidylether, or a bis-or poly-epoxy cross-linker such as 1,2,3,4-diepoxybutane or 1,2,7,8-diepoxyoctane.

To form an ether linkage the crosslinking agent is preferably selected from formaldehyde, gluteraldehyde, divinyl sulfone and, in alkaline conditions, bis and poly epoxides. Preferably the crosslinker contains a hydrophobic hydrocarbon segment, e.g. 1,2,3,4,-diepoxybutane, or most preferably 1,2,7,8-diepoxyoctane.

To form an ester linkage the cross-linking agent is preferably selected from polyhydric alcohols, carbodiimides, polyanhydrides, carboxylic acid chlorides and, in acid conditions, bis and poly epoxides. Preferably the crosslinker contains a hydrophobic hydrocarbon segment, e.g. 1,2,3,4,-diepoxybutane, or most preferably 1,2,7,8-diepoxyoctane.

An amide linkage is preferably formed using a cross-linking agent selected from carbodi-imides in the presence of amines, carboxylic acid anhydrides and chlorides (with de-acetylated HA), and diisocyanates.

An amine linkage is preferably formed using a cross-linking agent selected from an epoxide, or glutaraldehyde with a reducing agent, in the presence of amino groups in deacylated HA.

An imino linkage (schiff base bond) may be formed using glutaraldehyde in the presence of amino groups in deacylated HA.

A sulfone linkage is preferably formed using a sulfonyl chloride.

In one embodiment of the present invention, the different functional bonds may be formed sequentially, in a multi-step process, which may be achieved either by using a different cross-linking agent for each stage or by using the same cross-linking agent at each stage and adjusting the reaction conditions to control the specific cross-linking reaction required.

Thus, to achieve multiple, e.g. double, cross-linking in a step-wise manner according to the present invention a first cross-linking reaction is carried out, for example using one of the methods described below. When this is complete, or has progressed as far as required, a further cross-linking agent is added to the reaction mixture to effect the second cross-link. The further cross-linking agent may be the same or different from the first. When a different cross-linking agent is employed it will generally be selected such that without changing the reaction conditions, it will form a different type functional bond. However, when the same cross-linking agent is employed to form both cross-links, the reaction conditions should be adjusted accordingly in order to form a different type of bond. Those skilled in the art will readily be able to select an appropriate cross-linking agent and the appropriate reaction conditions to form the desired bond.

For the avoidance of doubt, it is noted that if the same cross-linking agent is used under the same reaction conditions at each step, this will result in only one type of linkage, i.e. it will give a single cross-linked product, albeit produced in two or more stages.

It will be appreciated that when the two or more functional bonds according to the present invention are formed sequentially, i.e. in a multi-stage reaction, the cross-link formed in the first stage of the reaction should be sufficiently strong to withstand the reaction conditions needed to form the second or subsequent cross-link(s). Thus, the stronger of the two (or more) bonds should be formed first. This will be readily apparent to the skilled worker and if necessary can be determined by means of routine experimentation.

Thus, when the cross-links are to be formed via hydroxyl and carboxyl groups it will be recognised that the first-stage cross-linking should be effected via the hydroxyl groups to give an ether linkage and the second-stage cross-linking will then be effected via the carboxyl groups, to give an ester link.

An ether bond may be formed using an epoxide crosslinker under alkaline conditions, preferably at a pH of 10 or more or, providing the polymers to be cross-linked do not contain amino groups, using glutaraldehyde as the crosslinking agent under acid conditions e.g. pH4 or less. An ester bond may be formed with an epoxide crosslinker under acid conditions e.g. pH4 or less.

Thus, for example, a first cross-linking reaction to form an ether linkage may be carried out using an epoxide such as 1,2 7,8-diepoxyoctane under alkaline conditions, preferably at a pH of 10 or more, for example in the range of pH 10 to pH12. A second cross-linking reaction to form an ester linkage may subsequently be effected employing the same cross-linking agent, and adjusting the pH of the reaction medium to pH4 or less, for example in the range pH 4 to pH2. Alternatively different cross-linking agents may be used in each step, in which case it may not be necessary to adjust the reaction conditions. Thus for example a first cross-linking reaction may be carried out using glutaraldehyde under acidic conditions to form an ether link, followed by reaction with an epoxide cross-linker also under acid conditions to form an ester link.

The concentration of HA in relation to the total polymer employed (i.e. HA+second+subsequent polymer, herein referred to as HA/polymer composite) will generally be in the range 1 to 99% e.g. 5 to 95%. Preferably the concentration of HA in the HA/polymer composite is at least 50%, and may be up to 99% e.g. 90% HA.

The ratio of cross-linking agent to total polymer (HA+ second polymer) employed at each stage of this process will generally be in the range 1:10 to 10:1 by weight.

The individual cross-linking reactions may be carried out according to methods known generally in the art.

Thus, the HA and second polymer utilised as the starting materials may be in the form of a film or in solution. An HA/second polymer film may be obtained by mixing HA and the required second polymer in aqueous solution and drying said solution to form a film. When such a film is employed, this may be suspended in a suitable solvent together with a cross-linking agent. The reaction medium preferably comprises an organic solvent such as acetone, chloroform, or an alcohol e.g. ethanol, or isopropanol, admixed with an aqueous acidic or alkaline solution. An acidic solution preferably has a pH of 4 or less and an alkaline solution preferably has a pH of 10 or above. The crosslinking reaction suitably takes place at a temperature in the range of 15 to 30° C. e.g. ambient temperature.

Preferably, when an HA/polymer film is employed as starting material, an ether cross-link is first formed with either epoxide under alkaline conditions or, providing the HA/polymer film does not contain free amino groups, with glutaraldehyde under acid conditions, followed by formation of an ester cross-link using epoxide under acid conditions. When an HA polymer/film contains amino groups a schiff base with an imino linkage can be formed using glutaraldehyde under acid conditions. This imino linkage can be converted to an amine linkage using a reducing agent.

Alternatively, the cross-linker may be added to an aqueous acidic or alkaline solution of HA and a second polymer. Under acidic conditions the pH of the starting solution is preferably pH4 or lower and for an alkaline solution the pH is preferably pH10 or above. The concentration of total polymer, i.e. HA plus other polymer in the solution is suitably in the range 1 to 10% w/w. The reaction may be effected at a temperature in the range of 15 to 50° C. The time for completion of the cross-linking reaction may in general vary from about an hour to a few days. Preferably, when a solution of HA and a second polymer is employed an ether cross-link is first formed with an epoxide under alkaline conditions, followed by formation of an ester cross-link using an epoxide (preferably the same epoxide as in the first step) under acidic conditions.

In a further method a solution of HA and second polymer may be subjected to a first cross-linking reaction, the intermediate product dried to form a film and said film subjected to a further cross-linking reaction as described above to give a double cross-linked product in the form of a film. Preferably, to obtain a double cross-linked HA derivative according to this procedure, an ether cross-link is first formed with an epoxide under alkaline conditions, followed by formation of an ester cross-link using an epoxide (preferably the same epoxide as in the first step) under acidic conditions.

In another embodiment of this invention, multiple cross-linking of HA with a second polymer, in particular double cross-linking, may be effected in a single step reaction, by contacting HA and the second polymer simultaneously with two different cross-linking agents, suitable for cross-linking two different functional groups under the same conditions. Thus, for example, to form both ether and ester groups in a single step HA and a second polymer may be contacted with a mixture of glutaraldehyde and 1,2,7,8-diepoxyoctane.

The ratio of cross-linking agent to total polymer (HA plus second polymer) employed at each stage of this process will generally be in the range 1:10 to 10:1 by weight.

The precise nature of the product may be varied by appropriate selection of reaction conditions so as to control the degree of cross-linking and hence the properties of the product. Factors which influence the degree of cross-linking and hence the nature of the final product include the form of the HA starting material employed, the nature of the second polymer, the feeding ratio of cross-linking agent to HA and second polymer, the reaction time, temperature and the pH. The product may be obtained in the form of a gel or film and may be clear or opaque. The water absorption capacity and biostability will vary depending on the precise nature of the product.

A product according to the invention may be obtained in the form of a film or sheet by employing the HA and other polymer starting materials in the form of a solution, film or sheet and carrying out the process without stirring. A non-cross-linked film or sheet comprising HA and a second polymer may be obtained by admixing HA and said second polymer in solution and drying to obtain a film or sheet. It will be appreciated that when HA plus polymer is employed in the form of a film or sheet, this will absorb water when placed in aqueous solution, such as PBS buffer, and swell to form a gel. If desired, an intermediate film may optionally be formed after the first cross-linking step, as described above. The product may be clear or opaque, depending upon the degree of cross-linking and the nature of the other polymer (s) to which HA is cross-linked. Thus for example cross-linking of HA with a polymer such as PVA can result in an opaque product in film or sheet form. Highly cross-linked HA/polymer products are generally opaque and may even be white in colour.

A product according to the invention in the form of a gel may be obtained by hydration of a film, which may for example be prepared as described above. If necessary the film may be subdivided into small pieces to facilitate absorbtion of water.

To obtain a product according to the invention in the form of an opaque gel, the HA and other polymer starting materials may be employed in the form of a solution, film or sheet and the entire process effected with stirring and without forming a film at any stage.

Whichever cross-linking method is used, the completion of the reaction can be routinely controlled by methods well known in the art, for example, the reaction may be terminated by neutralising the reaction mixture and solvent precipitation to obtain a product with the desired degree of cross-linking.

The final product may be isolated from the reaction medium by conventional procedures.

It will be understood that when a product containing more than two different cross-links is required, this may be prepared by an appropriate combination of sequential or simultaneous cross-linking reactions as described above.

In a particular embodiment of this invention HA may be cross-linked with alginate. The alginate may be employed in the form of e.g. a solution of sodium alginate. Conveniently, the alginate and HA may be admixed to form a homogeneous solution prior to initiating the cross-linking reaction. Calcium ions may also be added to the reaction mixture, e.g. in the form of a calcium chloride solution, resulting in the formation of ionic cross-links.

The concentration of HA in the HA/alginate composite may be in the range 95–5%, and is preferably at least 50% e.g. up to 90%.

HA and alginate can be cross-linked via both hydroxyl and carboxyl groups, resulting in ether and ester cross-linking bonds. It will be appreciated therefore that when the cross-linking is effected in a step-wise manner, the ether bond should be formed before the ester bond. Preferably a first cross-linking reaction is effected using an epoxide cross-linker such as 1,2,7,8-diepoxyoctane, under alkaline conditions, followed by a second cross-linking reaction with an epoxide such as 1,2,7,8-diepoxyoctane under acidic conditions.

In this embodiment cross-linking can take place via hydroxyl and carboxyl groups present on both polymers, and thus the HA forms two different functional bonds (ether and ester) with the alginate. Other anionic polymers, such as carboxymethylcellulose and gellan gum, and other polymers possessing two different functional groups, can be double cross-linked with HA in a similar manner.

In the case of anionic polymers containing only carboxyl groups, such as polyacrylic acid, it will be appreciated that only a single cross-link will be formed with HA, via an ester linkage. A second cross-linkage, according to the present invention, may be formed between two molecules of HA, or between the cross-linked HA and a different polymer.

In another specific embodiment HA may be cross-linked with the non-ionic polymer polyvinyl alcohol (PVA). In this instance HA and PVA are cross-linked via hydroxyl groups, forming an ether bond and the HA is further cross-linked to another molecule of HA via carboxyl groups, forming an ester bond.

The HA and PVA may firstly be admixed in solution, which can be dried to give an HA/PVA film, which is not cross-linked. Crosslinking may be effected by the methods described above. Preferably cross-linking is effected in a step-wise manner, with formation of an ether cross-link between HA and PVA followed by formation of an ester cross-link between two molecules of HA. Preferably the ether bond is formed using an expoxide under alkaline conditions and the ester bond is formed using an epoxide under acid conditions. Advantageously the expoxide is 1,2, 7,8-diepoxyoctane.

In a yet further specific embodiment HA may be cross-linked with the biopolymer chitosan (CS). Chitosan is a linear polymer of anhydroglucosamine. Commercially available chitosan is in fact a mixture with chitin, the former being a deacetylated derivative of the latter. In this specification the term "chitosan" will be used to mean pure chitosan as well as mixtures thereof with chitin. In this embodiment chitosan forms an inter-penetrating network (IPN) with HA. Thus chitosan and HA are linked via their amino and hydroxyl groups respectively and the HA is cross-linked to a further molecule of HA via the carboxyl groups, forming ester bonds.

In this embodiment a non-cross-linked HA/chitosan film may be prepared prior to the first cross-linking reaction. If desired, glycerol or a low molecular weight polyethylene glycol may be incorporated into the film as a plasticiser. A non-cross-linked HA/chitosan film may be prepared by admixing a solution of HA with a solution of chitosan and drying to obtain a film. However a simple admixture of chitosan and HA will form a precipitate due to ionic complexation. We have found that precipitation may be avoided by addition of sodium chloride or hydrochloric acid the mixture. Preferably sodium chloride is added at a concentration of 1 M to 2 M and hydrochloric acid at a concentration of 0.1 M to 0.5 M. This method can also be employed for admixing HA with other polycationic polymers and amino-containing synthetic polymers.

The first cross-linking reaction between HA and chitosan is preferably carried out on the non-cross-linked HA/chitosan film using an epoxide under alkaline conditions and the second cross-linking reaction to form an HA-HA cross-link is preferably effected using an epoxide under acid conditions. The epoxide is preferably 1,2,7,8-diepoxyoctane.

Other polymers having only one functional group can be cross-linked with HA in a similar manner to PVA and chitosan. In this case a second cross-link can be formed either between two molecules of HA or with a further polymer having an appropriate functional group.

In a preferred embodiment the present invention provides a process for preparing double cross-linked HA/polymer derivatives, said process comprising contacting HA and a second polymer with one or more cross-linking agents under conditions suitable for forming two different bonds between the HA molecules and said second polymer. Preferably the cross-linking reactions are effected sequentially. Thus, the two-stage process according to the invention comprises:
(a) cross-linking HA with a second polymer via a first functional group and subsequently
(b) further cross-linking the product of (a) via a second functional group, wherein said first and second functional groups represent different chemical entities.

Cross-linked HA/polymer derivatives prepared according to the present invention contain at least two different types of cross-linking bonds, for example both ether and ester bonds.

It is believed that multiple (e.g. double) cross-linked HA/polymer derivatives prepared according to the present invention are novel. Thus, in a further aspect the present invention provides multiple cross-linked HA/polymer derivatives (i.e. HA cross-linked to one or more polymers and optionally to other HA molecules, via two or more different functional bonds) obtainable by the process described hereinbefore.

In a further aspect the present invention provides HA cross-linked to one or more polymers other than HA wherein the HA and said polymer(s) are cross-linked by at least two different types of bond. In particular the present invention provides HA cross-linked to a second polymer wherein HA and said second polymer are cross-linked by two different types of bond.

The present invention also provides HA cross-linked to one or more polymers other than HA wherein the HA is cross-linked to said polymer(s) and to other molecules of HA by at least two different types of bond.

Double-cross-linked HA/polymer derivatives according to the present invention may have a degree of cross-linking in the range 10 to 50%, eg 15 to 30, preferably 20 to 25% (where 100% is represented by cross-linking of all OH groups at the C6 position and all COOH groups at the C5 position). The degree of cross-linking may be measured by elemental analysis or solid state NMR analysis. The ratios of the different functional bonds in the product will vary depending on the types of functional bonds present and the reaction conditions used to form them. For a double cross-linked product containing ether and ester bonds the ratio of these bonds may vary from 50:50 to 95:5, eg 60:40 to 80:20 ether:ester bonds.

In general a product according to the present invention has a greater degree of cross-linking, that is to say, a denser network of cross-links than does a single cross-linked HA/polymer derivative. A higher degree of cross-linking has been found to reduce the water absorption capacity of the cross-linked HA, resulting in greater stability in aqueous solution. In addition double cross-linked HA has been found to exhibit greater stability against degradation by hyaluronidase, and against degradation due to free radicals, indicating an increased biostability. As indicated above the biostability of the final product will depend, in part, on the nature of the other polymer(s) to which HA is cross-linked. The second and any subsequent polymer should therefore be chosen according to the properties desired, and this will be within the capability of the skilled worker.

An opaque product according to the present invention generally has a higher degree of cross-linking and hence lower water absorption capacity and greater stability, than a clear product. Such products are suitable for long term implantation.

A clear product e.g. a clear film, according to the present invention has higher water absorption capacity than an opaque product, but is nevertheless not water soluble, and such products are particularly suitable for dermal implants, wound healing (absorption of exudate) and resorbable short-term implantation.

The multi-step process described above is preferred when a highly cross-linked product with low water absorption capacity is desired. Simultaneous cross-linking generally results in a water-insoluble product, but with higher water absorption capacity than a product prepared using a multi-stage (e.g. two stage) process under similar cross-linking conditions.

Furthermore it has been found that using a first cross-linked HA/polymer film as starting material for the second cross-linking step provides a product (which may be in film form or may be converted into a gel) with lower water absorption capacity than a double cross-linked HA/polymer product prepared from an HA/polymer solution under similar cross-linking conditions (i.e. with no intermediate film formation). Indeed it has been found that the water absorption capacity of the resulting products can vary from 400% to 1000% for film and gel starting materials respectively.

Cross-linked HA derivatives according to the present invention may be used in a variety of pharmaceutical, medical (including surgical) and cosmetic applications.

Thus, they may for example be useful in promoting wound healing, e.g., as a dermal wound dressing.

They may also be useful in preventing adhesion e.g. preventing tissue growth between organs following surgery.

Crosslinked HA derivatives according to the present invention may also find application in the ophthalmic field e.g. for vitreous fluid replacement, as corneal shields for delivery of drugs to the eye or as lenticules.

Crosslinked HA derivatives according to the present invention may also be useful in surgery, for example as solid implants for hard tissue augmentation e.g. repair or replacement of cartilage or bone, or for soft tissue augmentation, as breast implants, or as coating for implants intended for long term use in the body, such as breast implants, catheters, cannulas, bone prostheses, cartilage replacements, mini pumps and other drug delivery devices, artificial organs and blood vessels, meshes for tissue reinforcement, etc. They may also be used as joint lubricants in the treatment of arthritis.

A further use for the derivatives of the present invention is in the delivery of therapeutically active agents including in any of the aforementioned applications. Therapeutically active agents may be chemotherapeutic agents or biologically active factors (e.g. cytokines) and include anti-inflammatory agents, antibiotics, analgesics, anaesthetics, wound healing promoters, cystostatic agents, immunostimulants, immunosuppressants and antivirals The therapeutically active factors may be bound, either physically or chemically, to the cross-linked HA derivative by methods well known in the art.

The cross-linked HA derivatives may be used in a variety of forms including membranes, beads, sponges, tubes, sheets and formed implants.

The invention will now be further illustrated by the following non-limiting examples.

The following procedures were used to measure the stability of the products.

Methodology

Water Absorption Capacity Assessment 20 mg ($W_d$) of each dried cross-linked samples were immersed in PBS formulation buffer solution for 24 hours to get a fully swollen gel. The wet gel was filtered off and the residual water at the surface was removed using tissue paper. The wet gel was weighed to give $W_s$. Thus the water absorption capacity (WAC) (%) can be calculated according to the following formula:

WAC(%)=(Ws—Wd)/Wd×100

Resistance to Hyaluronidase Digestion 20 mg cross-linked HA was suspended in 6 ml PBS buffer solution (pH=7.2) containing 1000 U hyaluronidase and incubated at 37 degree C. for 24 hours. After that, the film was removed and rinsed using PBS buffer and all the rinsing solution was collected to obtain total 10 ml solution. This solution was boiled for 30 minutes to get hyaluronidase precipitation. The solution then was centrifuged at 4000 rpm/10 minutes. The supernatant solution was made up to 25 ml using PBS solution in a volumetric flask. The HA concentration was measured using Carbazole assay.

The HA weight loss due to hyaluronidase digestion can be calculated using the following formula:

HA weight loss (%)=[HA]×25/[HA]o×100 in which, [HA] is the concentration of HA, [HA] is the original HA content (mg).

Resistance to Free Radicals

Ferton agents were used to create free radicals, which were formed by 25 microliter 0.1 ascorbic acid and 0.25 microliter 0.1 M $H_2O_2$ in 5 ml PBS solution. 20 mg of sample was added to this solution. The digestion time was 24 hours at 37° C. After this, the film or gel was removed and rinsed using PBS buffer and all the rinsing solution was collected to obtain total 25 ml using PBS solution in a volumetric flask. The HA concentration was measured using Carbazole assay. The HA loss was calculated using the same formula as hyaluronidase digestion.

EXAMPLE 1
Preparation of Cross-linked HA/PVA

1% HA and 5% PVA water solution was prepared respectively and mixed together to give a homogeneous HA/PVA solution with varied HA composition (see Table 1). The solution was cast in a petri-dish and dried for 4 days to obtain a film.

The resulting film was suspended in a mixture of $CHCl_3$ solvent/acidic or alkaline solution/1,2,7,8-diepoxyoctane or glutaraldehyde cross-linker. The cross-linking reaction was effected at room temperature for a fixed time (24 hr). A further amount of cross-linking agent was added, and if necessary the pH was adjusted, and the mixture was allowed to stand at room temperature for a further 24 hours, to effect the second cross-linking reaction. The detailed cross-linking conditions are shown in Table 1. After the cross-linking, the samples were washed with IPA and acetone for three times, immersed into IPA/deionised water (60/40) overnight and then washed with acetone and dried in a 37° C. oven to get a constant weight.

TABLE 1

Formation of Cross-linked PVA-HA (CPH)

| Samples | HA wt % | Cross-linker 1st/2nd | pH | Temp | Time | WAC % mean |
|---|---|---|---|---|---|---|
| CPH-2 | 10% | E | OH– | RT | 24 h/24 h | 280 |
| CPH-3 | 10% | E/E | H+/OH– | RT | 24 h/24 h | 340 |
| CPH-4 | 10% | E/E | OH–/H+ | RT | 24 h/24 h | 250 |
| CPH-6 | 20% | G/E | H+ | RT | 24 h/24 h | 600 |
| CPH-7 | 20% | E/E | H +/OH– | RT | 24 h/24 h | 580 |

TABLE 1-continued

Formation of Cross-linked PVA-HA (CPH)

| Samples | HA wt % | Cross-linker 1st/2nd | pH | Temp | Time | WAC % mean |
|---|---|---|---|---|---|---|
| CPH-8 | 20% | E/E | OH–/H+ | RT | 24 h/24 h | 480 |
| CPH13 | 50% | E/E | OH–/H+ | RT | 24 h/24 h | 258 |
| Reference Examples | | | | | | |
| CPH-1 | 10% | G | H+ | RT | 24 h | 300 |
| CPH-5 | 20% | G | H+ | RT | 24 h | Dissolved |
| CPH-9 | 30% | G | H+ | RT | 24 h | Dissolved |
| CPH-10 | 50% | G | H+ | RT | 24 h | Dissolved |
| CPH-11 | 50% | E/E | OH– | RT | 24 h/24 h | 3117 |
| CPH-12 | 50% | E/E | H+ | RT | 24 h/24 h | 1084 |

E = 1, 2, 7, 8-diepoxyoctane
G = glutaraldehyde
H+ represents a pH of about 4
OH– represents a pH of about 10
CPH-1, CPH-5, CPH-9, CPH-10, CPH-11 + 12 were all prepared using a single cross-linking step for comparative purposes.

TABLE 2

Biostability of crosslinked HA/PVA against hyaluronidase digestion

| SAMPLES | HYALURONIDASE DIGESTION HA WEIGHT LOSS(%) |
|---|---|
| CPH-12 | 43.3 |
| CPH-13 | 11.2 |

EXAMPLE 2
Double Cross-linked HA-alginate Film

Double cross-linked HA/Alginate film with different HA composition was prepared according to the method described below. Calcium ion solution with different concentration was used as an extra-ionic cross-linking.

Method

A 2% sodium alginate solution in deionised $H_2O$ was prepared and combined with a 1% sodium hyaluronate in phosphate buffered saline (HA) to give a homogenous HA/sodium alginate solution. The proportions and concentrations of the HA and sodium alginate in the solution can be varied depending on the characteristics required in the final film. The homogenous solution, approximately 10 ml, was poured into a petri dish and calcium chloride solution added. This was left approximately 1 hour during which ionic complexation occurred. The resulting HA/alginate slab was washed three times with deionised $H_2O$ to remove any unbound calcium. The polymerised HA/Alginate was allowed to dry in the fume cupboard for 72 hours. The resulting film was suspended in a solvent/alkaline solution. A volume of cross-linker, 1,2,7,8-diepoxyoctane was added and the reaction allowed to proceed at room temperature. The time for the cross-linking reaction can be varied between 1 hours and 48 hours. The film was suspended in an acidic solvent solution and a further volume of cross-linker, 1,2,7,8-diepoxyoctane added. The reaction was allowed to proceed at room temperature for between 1 hour and 48 hours. The resulting cross-linked film was washed with acetone/deionised $H_2O$ (3/2) solution three times followed by three washes with IPA/deionised $H_2O$ (3/1). The film was immersed in IPA/deionised $H_2O$ overnight. The film was allowed to dry in the fume cupboard.

TABLE 3

Formation of double-crosslinked Alginate (Alg)/HA (CAH)

| Samples | HA weight (%) | Cross-linker 1st/2nd | Calcium concn (N) | Reaction time (hours) | Temp (° C.) | Water absorption capacity (%) |
|---|---|---|---|---|---|---|
| CAH-1 | 90 | E/E | 0.25 | 24/24 | RT | 2543 ± 281 |
| CAH-2 | 90 | E/E | 0.5 | 24/24 | RT | 3342 ± 685 |
| CAH-3 | 50 | E/E | 0.25 | 24/24 | RT | 908 ± 47 |
| CAH-4 | 50 | E/E | 0.5 | 24/24 | RT | 1449 ± 110 |

TABLE 4

Biostability of double crosslinked Alginate/HA

| Samples | Hyaluronidase digestion HA weight loss(%) | Free radicals digestion HA weight loss(%) |
|---|---|---|
| CAH-1 | 53.04 ± 4.52 | 48.41 ± 12.78 |
| CAH-2 | 64.14 ± 4.51 | 50.41 ± 1.29 |
| CAH-3 | 66.17 ± 1.08 | 35.82 ± 3.11 |
| CAH-4 | 64.83 ± 1.74 | 33.03 ± 6.74 |

EXAMPLE 3
Preparation of Cross-linked HA/Chitosan (CS) Derivatives

HA/CS/glycerol film was prepared with different HA percentage. The cross-linker could be added either before the casting or after the casting. In this example, the dry HA/CS/glycerol film was used for cross-linking. Typically, as an example, a whole sheet of HA/CS (20% HA)(200 mg) was suspended in a container with 40 ml acetone/NaOH (pH=12) to soak for 1 hour, then 0.4 ml 1,2,7,8-diepoxyoctane was added for 24 hours reaction at room temperature. After this reaction, the pH was adjusted to pH=4~5 and another 0.4 ml (depending the concentration of HA) of 1,2,7,8-diepoxyoctane was added to proceed the second esterification for another 24 hours. After purification, it could be seen that the formed HA/CS film is tougher and more flexible in dry state than the sample without glycerol. It is transparent, colourless (in some cases, has a slight yellow colour depending on the cross-linking condition) and high water absorption.

Low molecular weight PEG could be used as an alternative to glycerol.

EXAMPLE 4
Preparation of Cross-linked HA/CS with 20% HA by Weight (Film)

2.0 ml HA (1% in PBS formulation buffer solution) and 8.0 ml CS (1% in 0.1 M HCl solution) was prepared respectively and mixed together to give a homogeneous HA/CS solution. The solution was cast in a petri-dish and dried in room temperature for one week to get a dried film. The dried film was paced in a vessel with 10 ml of mixed 1N NaOH water solution/acetone (30/70). 0.2 ml of 1,2,7,8-diepoxyoctane was added to react for 24 hours at room temperature. After the first cross-linking, another 0.5 ml of 1N HCl was added to keep the pH below 4. A further 0.2 ml of 1,2,7,8-diepoxyoctane was added to react for another 24 hours at room temperature. The film was removed and washed using 3/1 acetone/distilled water three times and 3/1 isopropanol (IPA)/distilled water another three times and stored in PBS formulation solution.

EXAMPLE 5
Preparation of Cross-linked HA/CS with 30% HA by Weight (in Gel Form)

HA dried sample was dissolved in 1.25 M NaCl solution to get 1.0% HA/NaCl solution. 5.0 ml of HA solution was mixed with 5.0 ml CS solution (1% in 0.1 M HCl) to get a homogeneous mixture. 0.2 ml glutaraldehyde and 0.2 ml 1,2,7,8-diepoxyoctane were added simultaneously to react 2.5 hours at 40° C. The formed gel was washed using 3/1 acetone/distilled water three times and IPA/distilled water (3/1) three times and stored in PBS formulation solution.

EXAMPLE 6
Preparation of Cross-linked HA/CS with 50% HA by Weight (Film)

Dried HA solid sample was dissolved in 0.1 M HCl solution to get 1% HA/HCl solution. 5.0 ml of this HA solution was mixed with 5.0 ml CS (1% in 0.1 M HCl) to get a homogeneous mixture. The solution was cast and dried at room temperature for one week to get a dried film. The film was cross-linked according to the same procedure as described in Example 4. Thus, a HA/CS biomatrix film containing 50% HA (based on feeding ratio) was obtained

EXAMPLE 7
Preparation of Cross-linked HA/CS with 60% HA by Weight (Film)

6.0 ml of 1% HA/1.25 M NaCl solution was mixed with 4.0 ml of 1% CS (in 0.1 M HCl solution) to get a homogeneous solution. The solution was cast and dried for one week at room temperature to get a dried film in which NaCl serves as a micro-pore inducer. The film was placed in a vessel and 10 ml of 1 N NaOH/acetone (30/70) was added to suspend the film. The cross-linking process was carried out according to the same procedure as described in Example 4. Finally a film with a porous structured surface was obtained.

EXAMPLE 8
Preparation of Cross-linked HA/CS with 80% HA by Weight (Film)

Dried HA solid sample was dissolved in 2.0 M HCl solution to get 1% HA/HCl solution. 8.0 ml of this HA solution was mixed with 2.0 ml CS (1% in 0.1 M HCl) to get a homogeneous mixture. The solution was cast and dried at room temperature for one week to get a dried film. The film was placed in a flask with a stopper and 10 ml 0.1 N HCl/acetone (3/7 in volume) was added to suspend the film. Then a mixture of 0.2 ml of glutaraldehyde and 0.2 ml 1,2,7,8-diepoxyoctane was added to react for 6 hours at room temperature. The film was purified according to the same procedure as described in Example 4.

EXAMPLE 9
Stability Test of Cross-linked HA/CS with Different HA Proportion by Weight A series of cross-linked HA/CS film with feeding ratios of HA varied from 20%, 30%, 40%, 50% to 60% were prepared according to the methodology as described in Example 6 to obtain samples CCH-5, 6, 7, 8 and 9. The samples were soaked in PBS formulation solution overnight and the wet films were weighed as an original weight (Wo). After storing in PBS solution for two weeks, the films were removed and the excess surface water was carefully removed using tissue paper and weighed again to get a remaining weight (Wr). Thus the weight remaining percentage can be derived from the following formulae: Weight remaining (%)=Wr/Wo× 100% The results are shown in Table 6.

TABLE 5

Comparison of single cross-linked and double cross-linked Chitosan(CS)/HA (CCH)

| Samples | HA weight (%) | Cross-linker 1st/2nd | Temp (° C.) | Time (hours) | pH | Water absorption capacity (%) |
|---|---|---|---|---|---|---|
| CCH-1 | 50 | E/E | RT | 24/24 | OH– | 321.8 |
| CCH-2 | 50 | E/E | RT | 24/24 | H+ | Dissolved |
| CCH-3 | 50 | E/E | RT | 24/24 | OH–/H+ | 280.5 |
| CCH-4 | 50 | E/E | RT | 24/24 | H+/OH– | Dissolved |

E 1, 2, 7, 8-diepoxyoctane; Feeding ratio of (HA + CS)/epoxide = 1/2 for each stage
OH– pH = 12; H+ pH = 4

TABLE 6

Stability of double cross-linked HA/CS (CCH)

| No | HA (w %) | Weight remaining (%) |
|---|---|---|
| CCH-5 | 20 | 92.0 |
| CCH-6 | 30 | 87.5 |
| CCH-7 | 40 | 81.2 |
| CCH-8 | 50 | 78.9 |
| CCH-9 | 60 | 80.5 |

What is claimed is:

1. A process for preparing multiple cross-linked derivatives of hyaluronic acid (HA), said process comprising covalently cross-linking HA to one or more polymers other than HA via two or more different functional groups, wherein said cross-linking is effected by contacting HA and a polymer other than HA with one or more chemical cross-linking agents so as to form two or more chemically distinct covalent cross-links between HA and said polymer.

2. The process according to claim 1, wherein said polymer is selected from a biopolymer or a synthetic polymer.

3. The process according to claim 1, wherein said synthetic polymer is selected from the group consisting of polyvinyl alcohol (PVA), polyethylene oxide (PEO), polypropylene oxide, copolymers thereof, polyacrylic acid, polyacrylamide, hydroxyl synthetic polymers, carboxyl synthetic polymers and hydrophilic synthetic polymers.

4. The process according to claim 2, wherein said biopolymer is selected from the group consisting of polypeptides, cellulose, cellulose derivatives, hydroxyethyl cellulose, carboxymethyl cellulose, alginate, chitosan, lipid, dextran, starch, gellan gum and polysaccharides.

5. The process according to claim 1, wherein said functional groups are selected from the group consisting of hydroxyl, carboxyl and amino.

6. The process according to claim 1, wherein said cross-linking is effected by means of two or more different bonds selected from the group consisting of ether, ester, sulfone, amine, imino and amide bonds.

7. The process according to claim 1, wherein said cross-linking agent is selected from the group consisting of formaldehyde, gluteraldehyde, divinyl sulfone, a polyanhydride, a polyaldehyde, a polyhydric alcohol, carbodiimide, epichlorohydrin, ethylene glycol, butanediol diglycidylether, diglycidylether, polyglycerol polyglycidylether, polyethylene glycol diglycidylether, polypropylene glycol diglycidylether, and a bis-or poly-epoxy cross-linker.

8. The process according to claim 1, wherein an ether bond is formed using a cross-linking agent selected from the group consisting of bis epoxides and poly epoxides under alkaline conditions.

9. The process according to claim 1, wherein an ester bond is formed using a cross-linking agent selected from the group consisting of bis epoxides and poly epoxides under acidic conditions.

10. The process according to claim 8, wherein said cross-linking agent is selected from the group consisting of 1,2,3,4-diepoxybutane and 1,2,7,8-diepoxyoctane.

11. The process according to claim 1, wherein an ether bond is formed using a gluteraldehyde cross-linking agent under acid conditions.

12. The process according to claim 1, wherein said cross-linking of each type of functional group is effected sequentially.

13. The process according to claim 12 comprising cross-linking HA to a polymer other than HA via a first functional group and subsequently further cross-linking the product via a second functional group, wherein said first and second functional groups represent different chemical entities.

14. The process according to claim 13, wherein HA is first cross-linked to a polymer other than HA via hydroxyl groups by formation of ether bonds and subsequently cross-linked either to said polymer or to another molecule of HA via carboxyl groups by formation of ester bonds.

15. The process according to claim 1, wherein said cross-linking of each type of functional group is effected simultaneously.

16. The process according to claim 1 for preparing double cross-linked HA.

17. The process according to claim 16 comprising:
(a) cross-linking HA with a second polymer via a first functional group and subsequently
(b) further cross-linking the product of (a) via a second functional group, wherein said first and second functional groups represent different chemical entities.

18. Multiple cross-linked HA obtainable by the process according to claim 1.

19. Hyaluronic acid (HA) cross-linked to one or more polymers other than HA, wherein said HA and said polymer(s) are cross-linked by at least two different types of bonds.

20. Hyaluronic acid (HA) cross-linked to a second polymer, wherein said HA and said second polymer are cross-linked by two different types of bond.

21. Hyaluronic acid (HA) cross-linked to a polymer other than HA, wherein said HA is cross-linked to said polymer and to another molecule of HA by at least two different types of bonds.

22. Cross-linked HA according to claim 18, wherein said cross-links are two or more selected from the group consisting of ether, ester, sulfone, amine, imino and amide bonds.

23. Multiple cross-linked HA according to claim 18 in the form of a film.

24. Multiple cross-linked HA according to claim 18 in the form of a gel.

25. A product comprising multiple cross-linked HA according to claim 18.

26. The process according to claim 1, further comprising covalently cross-linking HA to one or more polymers other than HA and to another molecule of HA.

* * * * *

UNITED STATES PATENT AND TRADEMARK OFFICE
CERTIFICATE OF CORRECTION

PATENT NO.      : 6,703,444 B2
DATED           : March 9, 2004
INVENTOR(S)     : Xiaobin Zhao, Catherine Alexander and Jane Elizabeth Fraser It is certified that error appears in the above-identified patent and that said Letters Patent is hereby corrected as shown below:

Title page,
Item [56], References Cited, OTHER PUBLICATIONS, "Survey of Organic" reference, please delete "Syntheisi" and insert -- Synthesis -- therefor;
Item [57], ABSTRACT,
Line 4, please delete "navel" and insert -- novel -- therefor.

Signed and Sealed this

Eighth Day of November, 2005

JON W. DUDAS
*Director of the United States Patent and Trademark Office*